United States Patent
Mintchev et al.

(10) Patent No.: US 9,066,877 B2
(45) Date of Patent: Jun. 30, 2015

(54) BEZOAR-FORMING UNITS FOR WEIGHT CONTROL

(75) Inventors: Martin Mintchev, Calgary (CA); Orly Yadid-Pecht, Calgary (CA); Michel Fattouche, Calgary (CA)

(73) Assignee: Eat Little Inc., Calgary, Alberta (CA)

( * ) Notice: Subject to any disclaimer, the term of this patent is extended or adjusted under 35 U.S.C. 154(b) by 515 days.

(21) Appl. No.: 12/936,558

(22) PCT Filed: Apr. 28, 2009

(86) PCT No.: PCT/CA2009/000598
§ 371 (c)(1),
(2), (4) Date: Dec. 7, 2010

(87) PCT Pub. No.: WO2009/132461
PCT Pub. Date: Nov. 5, 2009

(65) Prior Publication Data
US 2011/0082419 A1   Apr. 7, 2011

Related U.S. Application Data

(60) Provisional application No. 61/125,633, filed on Apr. 28, 2008, provisional application No. 61/130,592, filed on Jun. 2, 2008.

(51) Int. Cl.
*A61M 31/00* (2006.01)
*A61K 9/48* (2006.01)

(52) U.S. Cl.
CPC .................................... *A61K 9/4866* (2013.01)

(58) Field of Classification Search
USPC ........ 606/153, 143, 191–192, 157; 604/890.1
See application file for complete search history.

(56) References Cited

U.S. PATENT DOCUMENTS

| | | | |
|---|---|---|---|
| 4,485,805 A | 12/1984 | Foster, Jr. | |
| 4,607,618 A | 8/1986 | Angelchik | |
| 4,739,758 A | 4/1988 | Lai et al. | |
| 4,899,747 A | 2/1990 | Garren et al. | |
| 5,007,790 A * | 4/1991 | Shell | 424/451 |
| 5,234,454 A | 8/1993 | Bangs | |
| 5,750,585 A * | 5/1998 | Park et al. | 521/143 |
| 5,993,473 A | 11/1999 | Chan et al. | |

(Continued)

FOREIGN PATENT DOCUMENTS

| | | |
|---|---|---|
| CA | 2634132 | 7/2007 |
| CA | 2634614 | 7/2007 |

(Continued)

OTHER PUBLICATIONS

Charalabopoulos, K., et al. Phyto- and Trichobezoars as Foreign Bodies in the Gastrointestinal Tract. International Journal of Clinical Practice. 2007. pp. 169-170.

*Primary Examiner* — Quynh-Nhu H Vu
(74) *Attorney, Agent, or Firm* — Kyle R. Satterthwaite; Ryan W. Dupuis; Ade & Company, Inc.

(57) ABSTRACT

Bezoar-forming units for forming at least one temporary bezoar in a gastrointestinal organ of an animal, including a mammal, to fill a space in the said organ, are provided for weight control. The units include biodegradable fiber-based configurations of various length and shape having a first dimension and a second dimension; whereby when the bezoar-forming units are located in the given gastrointestinal organ, at least one temporary, permeable bezoar is formed.

12 Claims, 6 Drawing Sheets

(56) References Cited

U.S. PATENT DOCUMENTS

| | | |
|---|---|---|
| 6,271,278 B1 | 8/2001 | Park et al. |
| 6,449,511 B1 | 9/2002 | Mintchev et al. |
| 6,450,946 B1 | 9/2002 | Forsell |
| 6,453,907 B1 | 9/2002 | Forsell |
| 6,454,699 B1 | 9/2002 | Forsell |
| 6,460,543 B1 | 10/2002 | Forsell |
| 6,461,293 B1 | 10/2002 | Forsell |
| 6,535,764 B2 | 3/2003 | Imran et al. |
| 6,542,776 B1 | 4/2003 | Gordon et al. |
| 6,579,301 B1 * | 6/2003 | Bales et al. .................. 606/191 |
| 6,600,953 B2 | 7/2003 | Flesler et al. |
| 6,606,523 B1 | 8/2003 | Jenkins |
| 6,615,084 B1 | 9/2003 | Cigaina |
| 6,684,104 B2 | 1/2004 | Gordon et al. |
| 6,746,460 B2 | 6/2004 | Gannoe et al. |
| 6,981,980 B2 * | 1/2006 | Sampson et al. ............. 606/192 |
| 6,994,715 B2 | 2/2006 | Gannoe et al. |
| 7,066,945 B2 * | 6/2006 | Hashiba et al. ............... 606/191 |
| 7,120,498 B2 | 10/2006 | Imran et al. |
| 8,389,003 B2 * | 3/2013 | Mintchev et al. ............. 424/451 |
| 2004/0192582 A1 | 9/2004 | Burnett et al. |
| 2006/0020278 A1 | 1/2006 | Burnett et al. |
| 2006/0155311 A1 * | 7/2006 | Hashiba et al. ............... 606/153 |
| 2006/0212127 A1 * | 9/2006 | Karabey et al. ............. 623/23.75 |
| 2007/0038308 A1 | 2/2007 | Geitz |
| 2007/0156248 A1 | 7/2007 | Marco et al. |
| 2007/0276428 A1 * | 11/2007 | Haller et al. .................. 606/192 |
| 2008/0241094 A1 * | 10/2008 | Burnett et al. .............. 424/78.01 |
| 2008/0281355 A1 * | 11/2008 | Mayer et al. .................. 606/228 |
| 2010/0145316 A1 * | 6/2010 | Mintchev et al. .......... 604/890.1 |
| 2010/0185228 A1 * | 7/2010 | Tekulve et al. ............... 606/200 |

FOREIGN PATENT DOCUMENTS

| | | |
|---|---|---|
| WO | WO 98/51408 | 11/1998 |
| WO | WO 2004/056343 | 7/2004 |
| WO | 2006047882 | 5/2006 |
| WO | 2006122019 | 11/2006 |
| WO | 2007109904 | 10/2007 |
| WO | 2008074153 | 6/2008 |

* cited by examiner

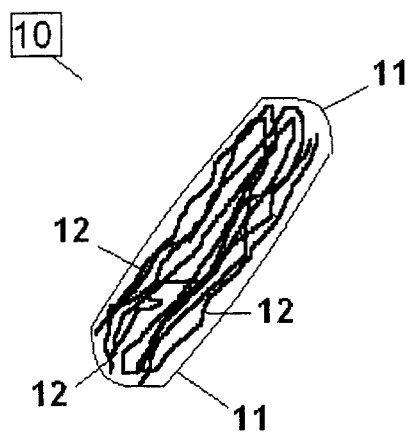
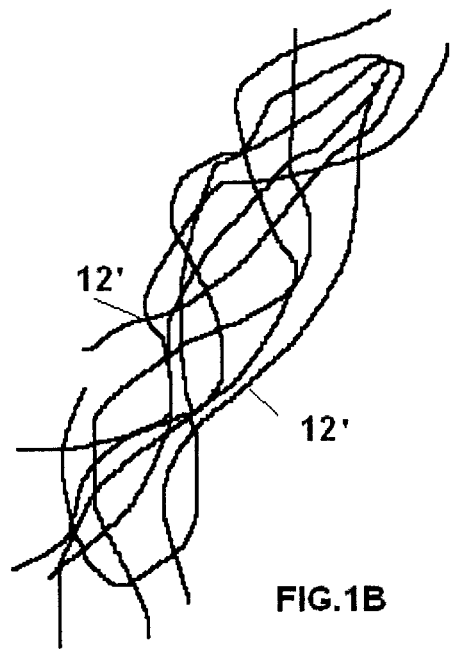
FIG. 1A
FIG. 1B
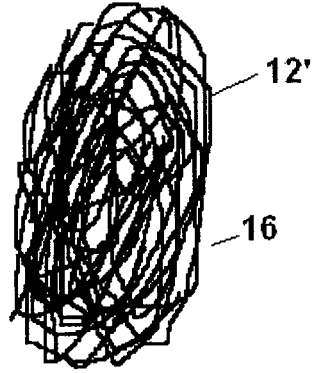
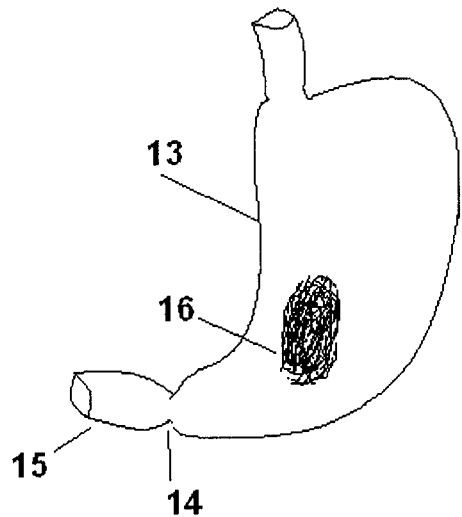
FIG. 1C
FIG. 1D

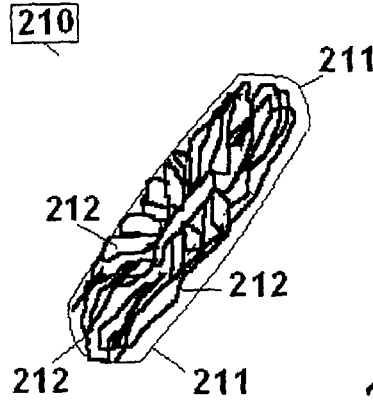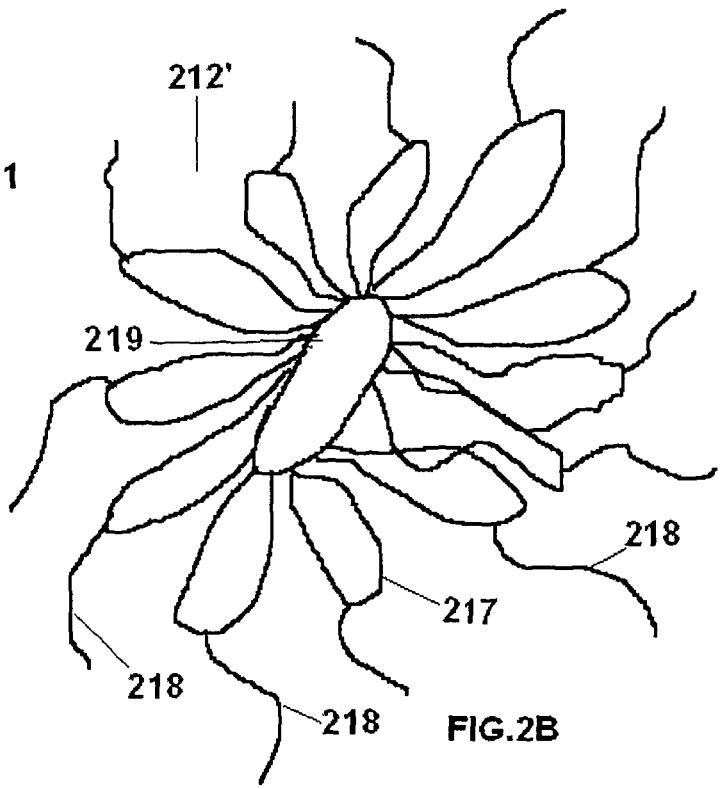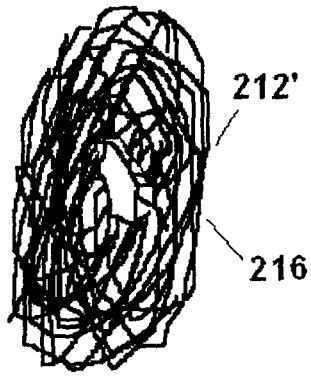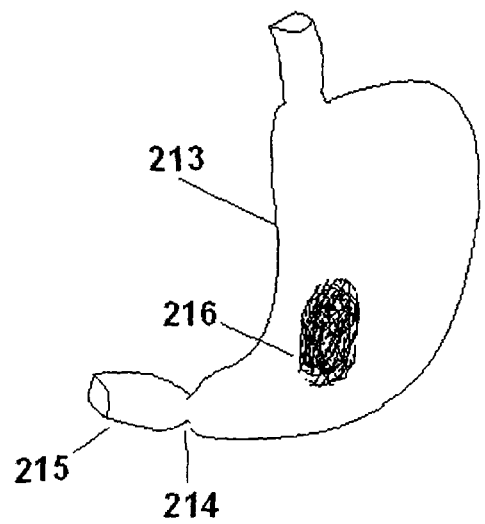
FIG.2A
FIG.2B
FIG.2C
FIG.2D

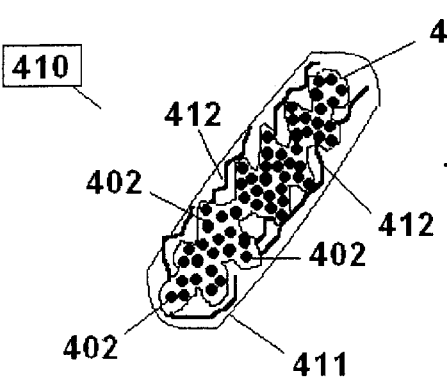
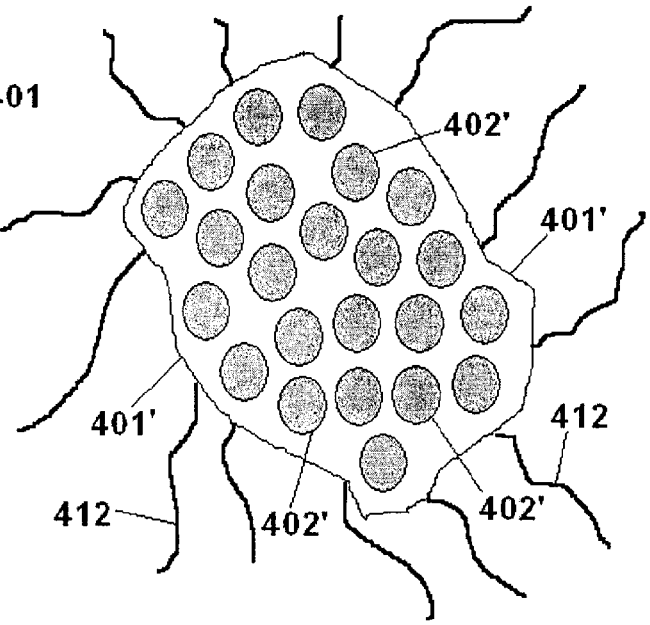
FIG. 4A　　　　　　　　FIG. 4B
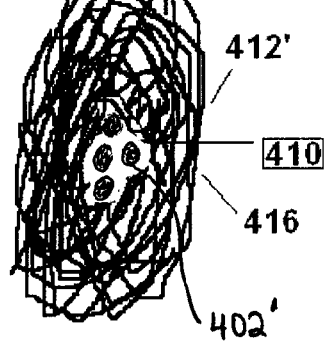
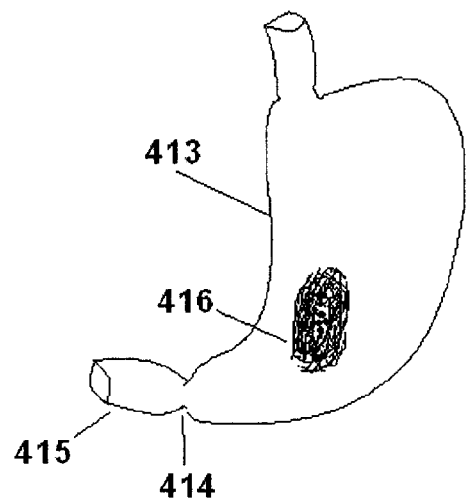
FIG. 4C　　　　　　　　FIG. 4D

BEZOAR-FORMING UNITS FOR WEIGHT CONTROL

FIELD OF THE INVENTION

The present invention relates to the field of dosage forms, and, more specifically, to bezoar-forming units useful for making temporary bezoars comprising fiber material useful for weight control and the treatment of obesity.

BACKGROUND OF THE INVENTION

Weight control and treatments for obesity have been the subjects of a large amount of suggested diets, treatments and procedures, including, in the most severe cases of morbid obesity, device implantations and/or direct surgical interventions. Recent comprehensive statistics from the National Institutes of Health (USA) indicates that more that 40% of Americans are obese, with more than 20% of these individuals being morbidly obese. In addition, it can be estimated that at least twice as many people are seeking to control their body weight, and/or are adhering to diets or other weight-control mechanisms. This is particularly significant since obesity has been implicated as a leading cause of various clinical conditions, including cardiovascular diseases and diabetes.

Six major streams of research and development related to new treatments for obesity are currently available: (1) diet regimens, and diet-related supplements and treatments; (2) pharmacological treatment using specifically developed medications; (3) gastric stimulation using implantable electronic devices; (4) invasive surgical procedures related to gastric reduction; (5) intragastric balloons or bezoars for reducing gastric volume and introducing a sensation of satiety and fullness; and (6) oral administration of cellulose or polymeric-based substances, which expand in the stomach and preclude their expulsion through the pylorus with the process of natural gastric peristalsis, thus introducing sensation of fullness and satiety. These expanded polymeric substances subsequently disintegrate chemically to allow for their expulsion from the body with natural gastrointestinal peristalsis.

Currently, there are very large numbers of various diets, diet supplements, diet regimens, and combinations thereof, and their numbers are growing dramatically. However, in many cases, these weight loss strategies do not work, or their success is very limited. The success of these techniques often varies widely between individuals, and they are often not sustainable.

Weight-loss related pharmacological treatment based on specifically developed and clinically-tested drugs and/or health supplements has also not been very successful. Numerous such therapies have been associated with various side effects, some of which are quite serious and life-threatening. Therefore, commercially-available and clinically-proven diets and/or anti-obesity drugs and health supplements have yet to be developed.

Recently developed techniques for gastric stimulation (see for examples U.S. Pat. Nos. 6,684,104, 6,615,084, 6,606,523, 6,600,953, 6,542,776, 6,535,764, and 6,449,511), involving surgical implantation of miniature microelectronic devices have been proposed as an avenue to tackle more severe cases of obesity, and particularly morbid obesity. The devices can administer electrical signals to the stomach and adversely affect normal propulsive gastric peristalsis. However, the procedures used for the positioning of the stimulating electrodes as well as the implantation of the device remain invasive, and the long-term effect of the treatment remains unknown both in terms of sustainability and safety.

Surgical procedures related to gastric volume reduction have been proven to be effective. However, they are invasive measures to address the problem of obesity. Mortality rates of procedures like gastric bypass or direct gastric volume reduction can reach 2%, have prolonged recovery periods, and can be quite expensive.

Bezoars are volume-taking phenomena occurring in the gastrointestinal tract of mammals, which are usually formed after systematic ingestion of hair (trichobezoars), some fruits or vegetables of high and specific fiber content such as persimmons (phytobezoars) or as a result of ingestion of substances and objects that cannot easily pass through the sphincters of the gastrointestinal tract (pica). Bezoars formed in the stomach and/or the intestines have been known to induce early satiety, anemia, and in extreme cases nausea, vomiting, bloating and gastro-intestinal obstruction (Charalabopoulos K et al., Phyto- and trichobezoars as foreign bodies in the gastrointestinal tract, International Journal of Clinical Practice, pp. 1741-42, 2006). Intragastric balloons positioned in the stomach either surgically or endoscopically to reduce the effective gastric volume mimic such bezoars and have been found effective in inducing early satiety and sensation of fullness, thus contributing to reduced food intake, which has been reliably related to sustainable weight loss (see for example U.S. Pat. Nos. 4,739,758, 4,485,805, 4,899,747, 5,234,454, 5,993,473, and 6,579,301). More recently, wireless control of volume-controlling devices in the stomach has been suggested (see for example U.S. Pat. Nos. 6,461,293, 6,454,699, 6,453,907, 6,460,543, and 6,450,946). Most recently, a "bow-tie" or "butterfly" intragastric bezoar has been suggested (WO/2006/122019, US Application 20060155311, U.S. Pat. No. 7,066,945) in contrast with the balloon shape proposed previously. The latter is launched endoscopically in the stomach and it is subsequently removed also invasively.

Although some of these techniques have shown to be effective in addressing the problem of obesity through intermittent gastric volume reduction from inside of the stomach thus avoiding surgical modification of gastrointestinal anatomy, they remain invasive and can be associated with serious and sometimes life-threatening side effects. The bezoars are positioned and removed invasively (in most cases endoscopically), and, more importantly, are built from non-permeable, impervious materials, and thus they are not permeable to liquids and gases, and are not disintegratable within the gastrointestinal tract. Therefore, they can potentially create life-threatening obstructions in the intestines, if they accidentally deflate, reduce volume or otherwise malfunction in the stomach and exit through the pylorus. These devices are not autonomously expandable, they are not of dynamically-manipulatable volume, and are not disintegratable from within the gastric lumen. Therefore, they are positionable and, most importantly, removable invasively (predominantly endoscopically), which limits the number that can be simultaneously present in the stomach. In addition, the lack of control over the dimensions of these bezoars triggers numerous other side effects in substantial number of patients, including vomiting, hypokalemia, abdominal pain, functional renal pain, gastroesophageal reflux, etc.

Most recently, the use of swellable polymers has been proposed to facilitate the reduction of gastric volume for treating obesity (see for example U.S. Pat. Nos. 5,750,585, 6,271,278, German Pat. No. NDN-050003290517, U.S. Patent Application No. 20040192582, U.S. Patent Application No. 20060020278). Compressed cellulose derivatives, or dehydrated hydrophilic polymers are introduced orally in the stomach, and expand to the point of not being able to pass through the pylorus, thus effectively achieving non-invasively what an intragastric balloon or another gastric volume-reducing device would achieve. However, in some instances, improper decomposition and/or degradation may lead to serious complications such as small bowel obstructions.

There is still a need for non-invasive techniques or products that can be easily used for prolonged and controlled reduction of gastric volume for use in facilitating weight loss, which address some of the problems encountered in the prior art. Our previous patent applications PCT/CA2007/000512 and PCT/CA2005/001693 offer some bezoar-based solutions to these problems. However, the bezoars discussed in these applications are multi-component, and are pre-formed. The aim of the present invention is to offer bezoar-forming units that can be utilized to form at least one volume-taking, permeable, temporary bezoar inside a given gastrointestinal organ, emulating the formation of trichobezoars and/or phytobezoars in mammals.

SUMMARY OF THE INVENTION

In one aspect, the invention is a method of forming at least one temporary bezoar inside a given gastrointestinal organ of an animal, including a mammal, which emulates a naturally occurring trichobezoar and/or phytobezoar with respect to its volume, permeability and means of expansion. Thus, a method for forming a temporary bezoar in a gastrointestinal organ of an animal, including a mammal, is provided, comprising:

administering a first unit comprising a first dissolvable container having at least one fiber, fiber-based configuration, or combinations thereof, contained therein, which at least one fiber, fiber-based configuration, or combinations thereof, unfolds from a first dimension to a second dimension once it is released from the container into the organ; and administering at least one second unit, the at least one second unit comprising a second dissolvable container having at least one fiber, fiber configuration, or combinations thereof, contained therein;

wherein the at least one fiber, fiber-based configuration, or combinations thereof, of the first unit is of a shape and size that allows the at least one fiber, fiber configuration, or combinations thereof, of the second unit to attach, connect or tangle thereto when released from the second container in the organ to form the temporary bezoar. The temporary bezoar emulates a trichobezoar and/or phytobezoar, which occur in nature. Thus, when the first unit and the at least one second unit are administered, at least one bezoar is formed. It is understood that the volume of the bezoar can be controlled by the subsequent and/or continued administration of additional units comprising fibers, fiber configurations, or combinations thereof, until satiety and/or reduced food intake is achieved.

In one embodiment, both of the units can be self-administrable (in the case of humans) or administrable autonomously or unaided, meaning the units are administrable without the need of any external positioning or manipulating device functionally attached to them, such as an endoscope. However, in another embodiment, a preformed bezoar is first made outside the body comprising fibers of appropriate length and configuration, which preformed bezoar can be administered endoscopically into the desired organ, and be maintained by continuous oral administration of additional units comprising fibers, fiber configurations, or combinations thereof.

Preferable, the fiber or the fiber configuration of a given unit has a first dimension, and can be retained in a dissolvable container such as a capsule capable of being easily swallowed or administered autonomously. Once the capsule has dissolved and the fiber or the fiber configuration is released in the stomach, the fiber or the fiber configuration will unfold to a second dimension. When the fiber or fiber configuration has expanded to the second dimension, it becomes sufficiently large so as to be temporarily retained in a given gastrointestinal organ. Other such fibers or fiber configurations are concurrently or sequentially administered, thus achieving the desired volume of the at least one temporary fiber-based bezoar for effective induction of early satiety and reduced food intake. In one embodiment, the dissolvable container can be any gelatin capsule known in the art, for example, a pH-sensitive 000 capsule made from Capsugel™, Greenwood, S.C., which disintegrates rapidly in the stomach but not in the esophagus, if the targeted gastrointestinal organ for bezoar formation is the stomach.

In one embodiment, the fibers forming the at least one bezoar are biodegradable over time. Thus, when the at least one bezoar is in the stomach, the stomach fluids will cause the formed fiber-based bezoar to slowly biodegrade, thereby releasing some sufficiently biodegraded fibers from the bezoar and into the stomach. In one embodiment, this volume loss in the bezoar may be compensated by continuously administering units comprising fibers, fiber configurations or combinations thereof, which fibers will continuously attach, connect or tangle to the remaining part of the bezoar, so that the desired volume of the said bezoar is controlled over a predetermined amount of time.

Generally, the fibers and the fiber configurations are of such length, shape and form that they can (a) form at least one "seed unit" in the stomach that is of a volume and shape that precludes its expulsion through the pylorus; (b) attach to an existing seed unit or the previously or concurrently administered fibers or fiber configurations; and (c) biodegrade after a certain predetermined period of time in gastrointestinal liquid. As used herein, "seed unit" generally means a first unit comprising a dissolvable container containing at least one fiber, fiber configuration, or combinations thereof, to which additional fibers and/or fiber configurations and/or both can attach, connect or entangle once the container dissolves and releases the at least one fiber, fiber configuration, or combinations thereof, in the desired gastrointestinal organ.

In one embodiment, the at least one fiber of the seed unit is of sufficient length, and the subsequently administered fibers are of adequate length and are administered in such time and in such quantity and frequency as to maintain at least one temporary permeable bezoar of known estimated volume in the stomach for the duration of the therapy. Preferably, the administration is with food, so that the pylorus is closed and there is sufficient time for the fibers to tangle together and form a bezoar.

In another embodiment, a two-dimensional fiber configuration is designed by interlacing one or more fibers to serve as an initial seed unit. Upon the administration of the seed unit containing the two-dimensional fiber configuration, subsequently or concurrently, there are administered additional units containing fibers, two-dimensional fiber configurations, or combinations thereof, of adequate length and shape are administered in such quantity and frequency as to maintain at least one temporary permeable bezoar of known estimated volume in the stomach for the duration of the therapy.

In yet another embodiment, a three-dimensional fiber configuration is formed by interlacing one or more fibers to serve as an initial seed unit. Upon the administration of the seed unit, subsequently or concurrently administered additional fibers, three-dimensional fiber configurations, or combinations thereof of adequate length and shape are administered in such quantity and frequency as to maintain at least one temporary permeable bezoar of known estimated volume in the stomach for the duration of the therapy.

Combinations between the three embodiments listed above are also possible. The volume of the formed at least one bezoar is maintained during the course of the therapy, but when the therapy is discontinued, it gradually biodegrades due to the biodegradability of the fibers that were used to form the bezoar. Thus, the at least one bezoar can be regarded as a temporary fiber-based bezoar that reduces the size of the gastrointestinal organ in which it is formed for the duration of the therapy.

Regardless of the particular embodiment, during the duration of the therapy a permeable fiber bezoar is formed in a gastrointestinal organ such as the stomach or the intestines. As the therapy progresses, some of the fibers within this bezoar disintegrate, but sequentially ingested fibers or/and fiber configurations compensate for this loss to dynamically maintain, increase or decrease the volume of the bezoar. It is possible to create several such bezoars during the course of the therapy. When the therapy is discontinued, the at least one bezoar biodegrades, falls apart and all parts or sections of it exit the gastrointestinal tract naturally and without creating any obstruction on their way.

In one embodiment, the fibers and the fiber configurations are made of specific biodegradable extruded, woven, knitted, braided or monofilament material, such as Vicryl™ (Ethicon), Monosyn™ (B Braun), catgut, oxidized regenerated cellulose, oxidized cellulose, oxidized cotton and the like, which have known well-established biodegradability patterns in the stomach and the intestines, are completely biocompatible upon ingestion, can have anti-inflammatory and antiseptic properties, and can be compressed to fit in an ingestible capsule.

In another embodiment, the fiber configuration comprises a plurality of sections, whereby each section is suitable for subsequently ingested biodegradable fibers or fiber configurations to attach or tangle into it, thus becoming an integral part of the bezoar. The biodegradable fibers can be made of an absorbable biocompatible material, which can include, but is not limited to, polycaprolactone, polyglycolide, polylactide, or combinations thereof (commercially available under the names Selecture PLL™ and Selecture VEH™ by Schering-Plough Animal Health Corporation). The biodegradable fibers can further be made, for example, from any absorbable suture known in the art such as Vicryl™, Monosyn™, catgut, PDS II™ (Ethicon, Cornelia, Ga.), or any other appropriate braided or monofilament absorbable suture. Soft monofilament material or material such as regenerated oxidized cellulose fiber, oxidized cellulose, oxidized cotton, or catgut could be utilized also to avoid possible mucosal injuries and to have anti-inflammatory and antiseptic effect.

In another aspect, a method of forming a temporary bezoar in a gastrointestinal organ of an animal, including a mammal, is provided, comprising:
 administering a bezoar-forming unit comprising a dissolvable container and a saclike member having a first dimension contained therein, the saclike member being made from a permeable material and comprising at least one fiber or fiber configuration attached thereto and at least one swellable agglomerate contained therein;
 dissolving the container once the bezoar-forming unit is positioned in the organ so that the saclike member is released in the organ; and
 allowing the at least one swellable agglomerate to swell such that the saclike member goes from the first dimension to a second dimension, thereby forming the temporary bezoar.

In one embodiment, the method of forming a temporary bezoar further comprises:
 administering at least one bezoar-enlarging unit, the at least one bezoar-enlarging unit comprising a dissolvable container having at least one fiber, fiber configuration, or combinations thereof, contained therein, whereby the at least one fiber, fiber configuration, or combinations thereof, of the bezoar-enlarging unit is allowed to attach, connect or tangle with the at least one fiber or fiber configuration of the bezoar-forming unit to form the temporary bezoar.

The saclike member can be made from permeable biodegradable mesh such as Vicryl™ Knitted Mesh by Ethicon, Curacel™ by CuraMedical, or Safil™ Mesh by B Braun and the mesh has radial fibers made, for example, from absorbable surgical suture such as Vicryl™, PDS II™ (Ethicon), catgut, oxidized cellulose, regenerated oxidized cellulose, oxidized cotton, or Monosyn™ (B Braun) woven therethrough. The saclike member is biodegradable, hence when it disintegrates, the saclike member loses its integrity due to the gastric peristaltic forces, and the agglomerates are released. In addition, the material can have anti-inflammatory and antiseptic properties, such as oxidized cellulose, which has been utilized as absorbable internal wound treatment.

In one embodiment, swellable agglomerates comprise a swellable material selected from the group consisting of a swelling bentonite, microcrystalline hydrogels, polyolefins and various mixtures thereof. Other swellable materials that could be used include, by are not limited to, other natural clays, polyvinyl alcohol, poly(ethyloxazoline), polyvinylacetate-polyvinylalcohol copolymers, poly(2-hydroxyethylacrylate), poly(2-hydroxyethylmethacrylate), polyacrylic acid, and copolymers thereof, polysaccharides, water soluble proteins, polynucleic acids, or a combination thereof. In another embodiment, each swollen agglomerate does not exceed 1 cm in diameter, so that such agglomerates can easily individually pass the pylorus and be expelled through the gastrointestinal tract after the disintegration of the saclike member. Furthermore, if desired, the agglomerates comprise a swellable material that is also biodegradable, thereby further facilitating each agglomerate passage through the intestines. It is understood that a variety of other biocompatible super-absorbent polymers known in the art can be used to form the agglomerates of the present invention, for example, polymers of poly(2-hydroxyethyl methacrylate) by Aldrich, Milwaukee, Wis., or of polyacrylamide, or of an appropriately cross-linked poly(acrylic acid) (for example, one produced by Wako Pure Chemical Industries, Japan) which expand adequately in low pH environment, but lose volume at higher pH environment (above 6).

In another embodiment, the temporary bezoar of the present invention can be formed outside the body to adequately large dimensions, and then be positioned endoscopically, rather than being gradually built using ingestible capsules containing fibers or fiber configurations. This approach may be preferred in order to make sure that the initial bezoar is securely formed and that it would stay in the stomach rather then exiting through the pylorus. This would be particularly useful for patients that have rapid gastric emptying and the formation of a bezoar by oral administration of fibers, fiber configurations, or combinations thereof cannot be easily achieved.

In yet another embodiment, the fibers forming the at least one bezoar in a given gastrointestinal organ can be impregnated with a certain medical substance, for example anti-inflammatory and antiseptic medications and antibiotics such as erythromycine, antifungal medications such as fluconasole, antiacid medication such as omeprazole, and the like, so that slow and continuous delivery of the said substance is provided.

Another embodiment of the invention addresses the issue of utilizing the formed at least one bezoar to absorb unwanted and/or harmful substances from the gastrointestinal liquid surrounding it. For example, impregnating or integrating the fibers utilized to form a gastric bezoar with chitosan can be employed for the absorption of lipids in the stomach prior to them entering the intestines to be absorbed by the body.

According to another broad aspect of this invention, there is provided a schedule for the administration of the various units so that after the formation of at least one temporary permeable bezoar the therapy becomes part of a weight-reduction diet leading to behavioral and lifestyle modifications needed to sustain weight loss for a substantial period of time after the therapy is discontinued. This schedule includes, but is not limited to, maintaining an active therapy with temporary permeable bezoars in the stomach for 2-3 months, during which period it is combined by an appropriately designed diet, which facilitates the said behavioral and lifestyle modifications. Subsequently, the temporary permeable bezoars disintegrate and leave the body naturally, but the behavioral and lifestyle modifications remain in place for a substantial post-therapy period. The administration of the units can be, but is not limited to, immediate bezoar formation and daily, weekly or monthly maintenance by administering appropriate number of bezoar-enlarging units comprising fibers, fiber configurations, or combinations thereof. These administration schedules are illustrated below by the means of example of bezoars lasting in the stomach for 80 days, which is used for illustrative purposes only. Bezoars can last in the stomach a wide range of days, for example, which is not meant to be limiting, from 1 to 120 days.

Immediate administration of the seed unit and at least one additional unit, or the bezoar-forming unit, can take place in one single day after the necessary patient-specific gastric volume reduction has been determined. For example, at least one bezoar can be formed if at least one seed unit comprising a three-dimensional multi-loop fiber configuration contained in a single capsule is ingested during a meal, immediately followed by swallowing multiple units contained in capsules, each containing as many independent 50-cm fibers as needed to achieve the desired volume of the at least one bezoar. The independent fibers will mix with the food in the stomach, and before the pylorus significantly opens will tangle with the seed unit, forming at least one bezoar of desired volume. Depending on the volume of the stomach of the particular patient, dozens of such units can be administered during the first day of the therapy with each meal. Subsequently, only a maintenance dosage is given, in which the number of ingested fibers and/or fiber configurations is about the same as the number of fibers initially administered. This dosage can be equally spread within the predetermined number of days in which an individual fiber loses about 75% of its tensile strength. As mentioned, the maintenance dosage can be daily, weekly, or monthly.

The orally administrable units of the present invention are preferably comprised of a dissolvable capsule known in the art. As soon as the unit is ingested, the capsule starts disintegrating. The time of disintegration of the capsule needs to be long enough so that the capsule is not disintegrated fully prior to reaching the organ of choice (e.g., the stomach) but short enough so that the implement is not expelled though the pylorus prior to the capsule disintegrating. For this reason, the preferable administration of the units comprising fibers is during meals, when the pylorus is closed.

The bezoars formed in the present invention affect satiety by reducing gastric volume from inside of the stomach through the creation of at least one volume-taking temporary gastrointestinal bezoar, which will reduce gastric volume resulting in early satiety and reduced food intake much similarly to naturally formed tricho- and phytobezoars.

In addition, there are provided optimization and safety measures for the implements of the present invention. The optimization measures can include, but are not limited to, any one or more of the following:

i. Designing the at least one seed unit using such fiber or fiber configuration that would allow the majority of subsequently administered fibers, fiber configurations, or combinations thereof to attach or tangle to it in order to form a bezoar;

ii. Utilizing an appropriate length of the administered fibers, fiber configurations, or combinations thereof, and administering them in appropriate time (for example, during meals), so that their formation of, or attachment to the at least one temporary bezoar is secured;

iii. Maintaining the subsequent administration of fibers, fiber configurations or combinations thereof in the course of the therapy, so that the formed bezoar is of desired volume to affect the eating habits of the patient and to reduce food intake without, however, inducing nausea, vomiting, anemia, or other abnormal and undesired consequences;

iv. Administering the fibers, fiber configurations, or combinations thereof in such way that the at least one bezoar is securely formed;

v. The units are comprised of such materials, which do not injure the mucosa in the gastrointestinal tract before or after disintegration.

vi. Designing the at least one fiber and/or fiber configuration in such manner that it fits precisely in the volume of a standard ingestible capsule, without any unutilized space in the said capsule when closed;

vii. The biocompatible, permeable bezoar formed by concurrently or sequentially administering of fibers, fiber configurations or combinations thereof made from biocompatible material that can attach, tangle or join together in aqueous solution such as gastrointestinal juice, and the means for disintegrating the bezoar so that it disintegrates into smaller pieces after a predetermined time in the stomach of an animal, including mammal. This disintegration is either intrinsic feature of the material used to form the bezoar, or is facilitated by an external substance (in a preferred embodiment this could be a specific volume of Coca-Cola or Coca-Cola-like drink, or Seltzer Soda administered over a specific period of time), or both. The disintegration of the temporary bezoar can typically occur between the first and the $120^{th}$ day post-formation.

viii. The safety measures can be of a wide variety, which can include, but are not limited to, designing the temporary bezoar in such way that it would pass gastrointestinal liquids of particular consistency while retaining its volume characteristics, segmenting the bezoar into smaller parts or sections, kept together by biodegradable material with shorter biodegradation lifespan than the seed of the bezoar itself, or by using a material which is slowly disintegratable in gastric juice, but is rapidly disintegratable in the small intestine, so that intestinal obstruction is prevented. If needed, the pH in the stomach can be maintained at a value providing slow disintegration using an appropriate medication. For example, acid reduction therapy using omeprazole (0.5 mg/kg daily) can maintain the pH value in the stomach between 4 and 5 rather than the normal value of 1.5-2, without any side effect for the duration of the therapy, or for the duration of the initial expansion of the temporary bezoar, until it reaches its final effective post-ingestion volume. As mentioned, the speed of disintegration can be facilitated by administering external substance either transorally or transnasally, for example Seltzer Soda and the like, containing sodium bicarbonate.

ix. Further, the safety measures include, but are not limited to, selecting a material for the fibers forming the temporary bezoar that does not injure or inflame the mucosa of the gastrointestinal tract prior to or after the disintegration of the formed bezoar. An additional benefit would be that these fibers have anti-inflammatory and antiseptic effect, which can help disorders like Crohn's disease, colitis, and irritable bowel syndrome.

In addition, there are provided patient-specific administration schedule for the device.

i. The administration schedule includes, but is not limited to, swallowing ingestible capsules containing fibers, fiber configurations or combinations thereof causing the formation of at least one artificial limited-volume temporary bezoar in the stomach in such way that the combined volume taken by these temporary gastric bezoars is specifically tailored to the gastric volume of the patients before the administration, so that the therapy does not modify the anatomy of the stomach when discontinued.

ii. The means for disintegrating the at least one temporary bezoar can be related to the material of the bezoar itself, or can be controlled by an external substance, such as, for example that is not meant to be limiting, sodium bicarbonate, Alka Setzer™, etc.

iii. The patient-specific administration schedule includes, but is not limited to, preliminary assessment of the gastric volume of the patient using barostat measurement, barium X-ray measurement, scintigraphy, fluoroscopy, or any other objective technique for assessing gastric volume, and sequentially or simultaneously administering a number of capsules which form temporary bezoars of limited and pre-determined volume in the stomach, so that a known composite bezoar volume is obtained, in such manner that the therapy is effective, but the stomach of the patient is not unnecessarily subjected to abnormal volume changes and stretching.

For purposes of summarizing the invention and the advantages achieved over the prior art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The present invention, both as to its organization and manner of operation, may best be understood by reference to the following description, and the accompanying drawings of various embodiments wherein like reference numerals are used throughout the several views, and in which:

FIG. 1A is a schematic view of one embodiment of a bezoar-forming unit according to the invention, where the fibers are in the first dimension and are packed in a swallowable capsule that would dissolve in the stomach.

FIG. 1B is a schematic view of the bezoar-forming unit of FIG. 1A in the second dimension as a result of the capsule disintegrating in the stomach and the fibers becoming loose.

FIG. 1C is a schematic view of the bezoar formation from the loose fibers that have attached or tangled together.

FIG. 1D is a schematic representation of the formed bezoar located in the stomach.

FIG. 2A is a schematic view of another embodiment of a bezoar-forming unit according to the invention, where a two-dimensional fiber configuration is used and it is in the first dimension.

FIG. 2B is a schematic view of the bezoar-forming unit of FIG. 2A in the second dimension.

FIG. 2C is a schematic view of the bezoar formation using the two-dimensional fiber configuration from FIG. 2B as a seed unit and having additional fibers or fiber configurations attached or tangled to it.

FIG. 2D is a schematic representation of the formed bezoar located in the stomach.

FIG. 4A is a schematic view of another embodiment of an orally administrable implement according to the invention, where an expandable container is utilized as a seed and it is in the first dimension (capsulated).

FIG. 4B is a schematic view the embodiment including an expandable container utilized as a seed in the expanded second dimension (post-administration and after its expansion in gastrointestinal liquid).

FIG. 4C is a schematic view of the orally administrable implement of FIG. 4A in the expanded second dimension after a bezoar around it is formed using the expandable container and the attached to it fibers as seed, and additional fibers or fiber configurations attached or tangled to it.

FIG. 4D is a schematic representation of the formed bezoar located in the stomach.

Figure 3A:
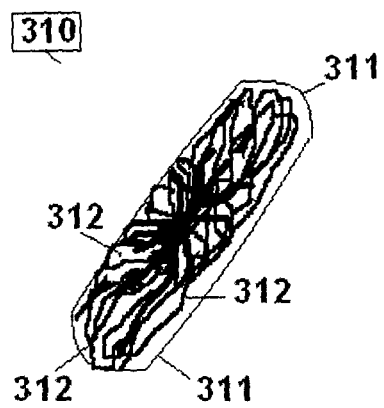
FIG. 3A is a schematic view of another embodiment of a bezoar-forming unit according to the invention, where a three-dimensional fiber configuration is used and it is in the first dimension.
Figure 3B:
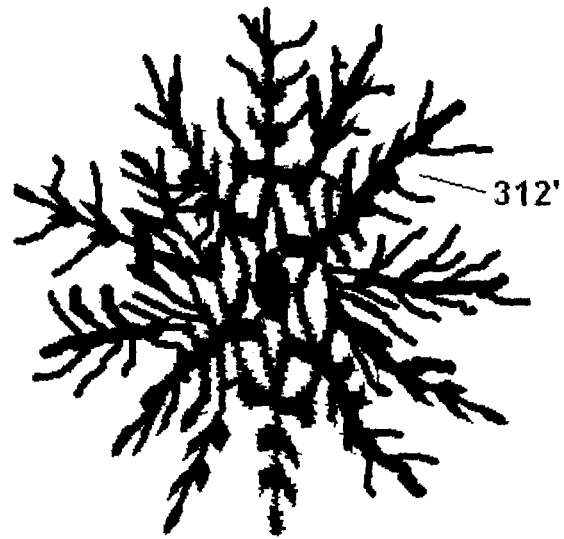
FIG. 3B is a schematic view of the bezoar-forming unit of FIG. 3A in the second dimension.
Figure 3C:
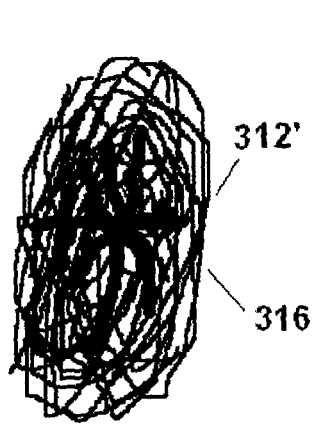
FIG. 3C is a schematic view of the bezoar formation using the three-dimensional fiber configuration from FIG. 3B as a seed unit and having additional fibers or fiber configurations attached or tangled to it.

In all these figures, the fibers, fiber configurations, or combinations thereof that are utilized may or may not be impregnated with specific medicinal substances for slow release, or with substances that can absorb unwanted substances from the gastrointestinal liquid in the organ where the at least one bezoar is formed.

DESCRIPTION OF THE PREFERRED EMBODIMENTS

The preferred embodiments correspond closely to the figures, and are discussed in detail herein.

In one embodiment, as shown in FIGS. 1A-1D, unit 10 comprises dissolvable capsule 11 and at least one sufficiently long fiber 12 packed therein in a first dimension (FIG. 1A). Upon administration in a given gastrointestinal organ, which may include but is not limited to the esophagus, the stomach, the small intestine, the colon, and the rectum, the capsule 11 dissolves and the at least one fiber 12 is released and unfolds or expands to form a second dimension fiber 12' in the said organ, thus establishing a seed unit for a bezoar formation (FIG. 1B). Upon further administration of a predetermined number of additional units 10, a fiber bezoar 16 is formed (FIG. 1C), which is illustrated also in FIG. 1D in the stomach 13, and is of sufficient size so that it cannot exit the pylorus 14 into the duodenum 15.

In another embodiment, as shown in FIGS. 2A-2D, the unit 210 comprises dissolvable capsule 211, encapsulating a two-dimensional fiber configuration 212 in its first dimension (FIG. 2A). Upon administration in a given gastrointestinal organ, which may include but is not limited to the esophagus, the stomach, the small intestine, the colon, and the rectum, the capsule 211 dissolves and the fiber configuration 212 unfolds or expands to a second dimension to form a second dimension fiber configuration 212'. The specific two-dimensional configuration shown here for illustrative purposes only (FIG. 2B) resembles a large daisy, with a center core 219 and loops 217 stemming from it, on which loose fibers 218 are also attached. Such configuration facilitates a bezoar formation 216 (FIG. 2C) either on its own or upon further administration of additional units comprising fiber configurations or loose fibers in a predetermined quantity and frequency. The formed fiber bezoar 216 is illustrated in FIG. 2D as located in the stomach 213 and is of such size that precludes it from exiting through the pylorus 214 and into the duodenum 215.

Figure 3D:
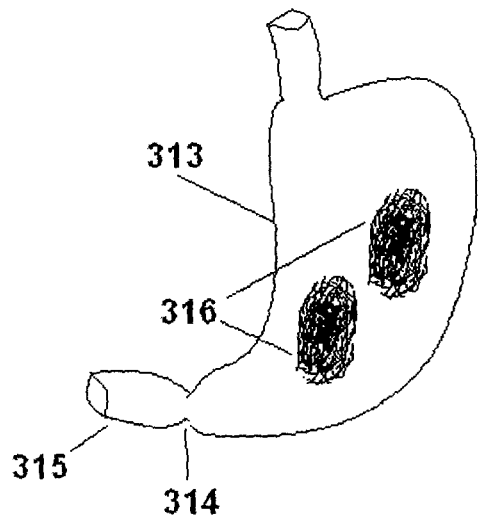
FIG. 3D is a schematic representation of two formed bezoars located in the stomach.

In another embodiment, as shown in FIGS. 3A-3D, unit 310 comprises dissolvable capsule 311, encapsulating a three-dimensional fiber configuration 312 in its first dimension (FIG. 3A). Upon administration in a given gastrointestinal organ, which may include but is not limited to the esophagus, the stomach, the small intestine, the colon, and the rectum, the capsule 311 dissolves and the fiber configuration 312 expands to a second dimension to form a second dimension fiber configuration 312'. The specific three-dimensional configuration shown here for illustrative purposes only (FIG. 3B) resembles a large three-dimensional snowflake. Such configuration facilitates a bezoar formation 216 (FIG. 3C), either on its own or upon further administration of such units or other units comprising fiber configurations or loose fibers continues in a predetermined quantity and frequency. It is understood that in some instances it might be desirable to form more than one bezoar at any given time to take up more space in the organ, such as the stomach. FIG. 3D shows two formed fiber bezoars 216 in the stomach 313 and are of such sizes that precludes them from exiting through the pylorus 314 and into the duodenum 315.

In another embodiment, as shown FIGS. 4A-4D, a bezoar-forming unit 410 comprises dissolvable capsule 411, encapsulating a three-dimensional permeable saclike member 401. Saclike member 401 contains a plurality of swellable agglomerates (e.g., swellable polymers) 402 and has radial outwardly-pointing fibers 412 attached to its outer surface. The saclike member 401 is illustrated in its first dimension in FIG. 4A. Upon administration in a given gastrointestinal organ, which may include but is not limited to the esophagus, the stomach, the small intestine, the colon, and the rectum, the capsule 411 dissolves and the saclike member 401 expands to a second dimension, saclike member 401' due to the swelling of the swellable agglomerates 402 to form expanded agglomerates 402'. The radial fibers 412' are now unfolded too. The specific three-dimensional configuration shown in FIG. 4B for illustrative purposes only forms a bezoar 416 (FIG. 4C), the volume of which may be further expanded and maintained upon further administration of units 10, 210, and/or 310, as shown in FIGS. 1, 2 and 3, in a predetermined quantity and frequency. The formed fiber bezoar 416 is illustrated in FIG. 4D in the stomach 413 and is of such size that precludes it from exiting through the pylorus 414 and into the duodenum 415.

Figure 5:
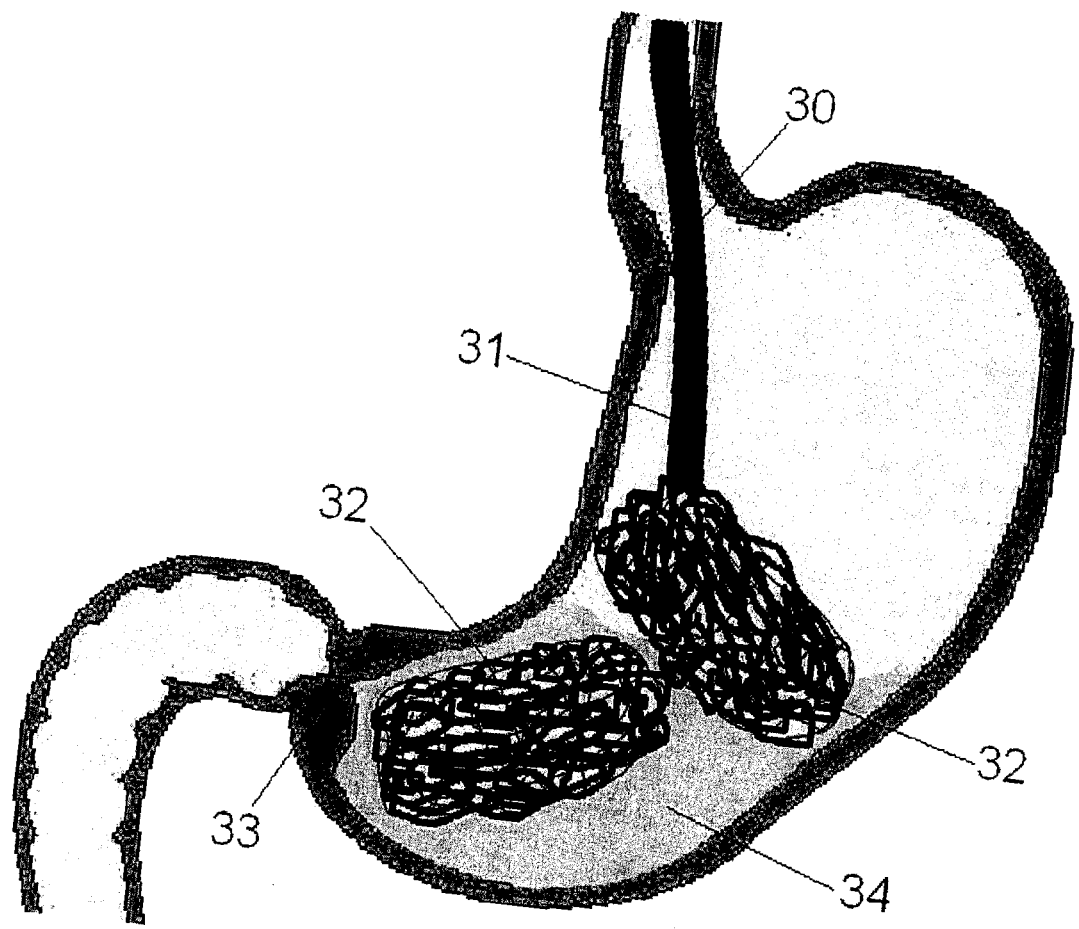
FIG. 5 is a schematic view of an embodiment of the implement of the present invention, which represents a seed bezoar that is pre-formed outside the body and is being positioned gastroscopically in the stomach. Another such bezoar (already positioned) is also shown.

In another embodiment, as shown in FIG. 5, a pre-formed fiber bezoar 32, according to any of the previous embodiments, is first formed outside the body and then is positioned invasively in the stomach 34 using an endoscope 30. Two such bezoars are illustrated in FIG. 5, one already positioned and the other in a process of being positioned, and each of them is of a size precluding its exit through the pylorus 33.

Figure 6:
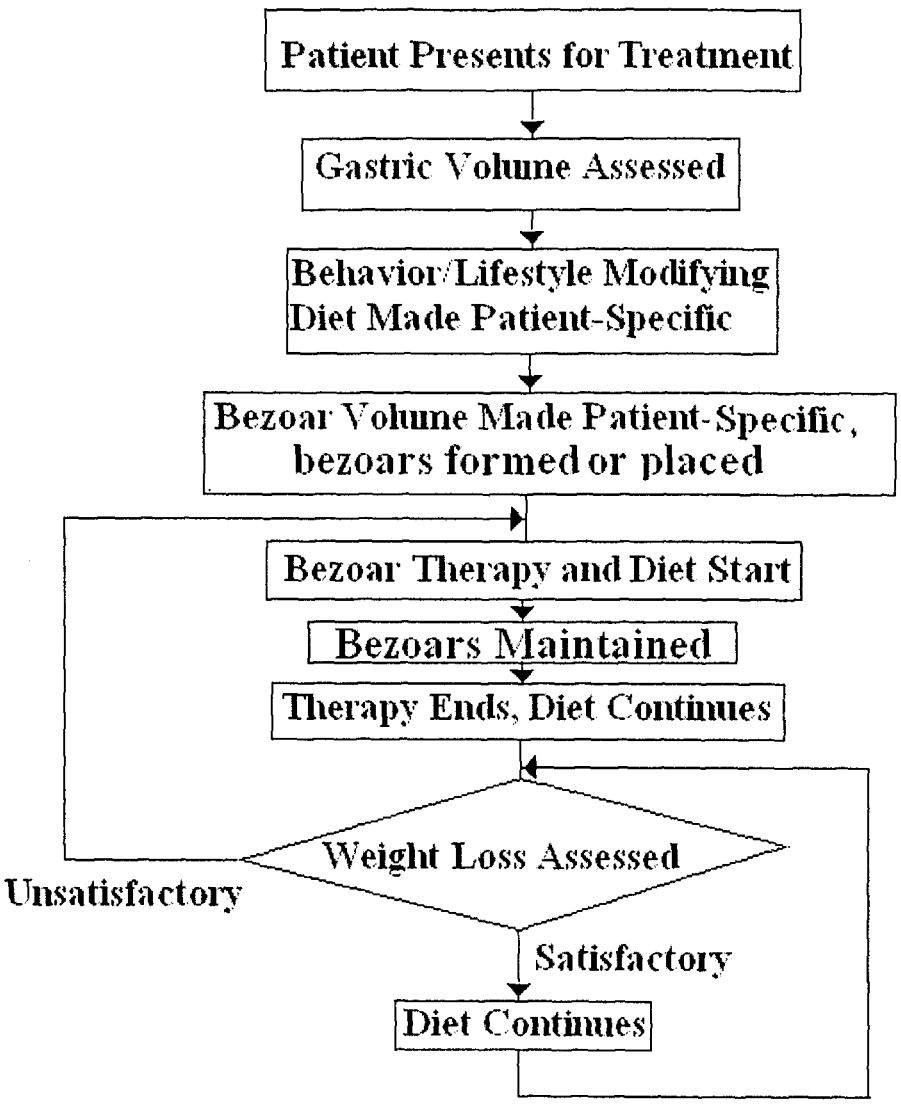
FIG. 6 represents a block-diagram of a possible administration schedule of an orally administrable implement of the present invention.

The flow chart, as shown in FIG. 6, illustrates a possible combined therapy and diet schedule that minimizes the utilization of bezoars for reducing food intake by combining the bezoar-induced early satiety with eating habits dietary modifications.

The dissolvable containers can be any gelatin capsule known in the art, for example, a pH-sensitive 000 capsule made from Capsugel™, Greenwood, S.C., which disintegrates rapidly in the stomach but not in the esophagus, if the targeted gastrointestinal organ for bezoar formation is the stomach.

The fibers and the fiber configurations can be made of specific biodegradable extruded, woven, knitted, braided or monofilament material, such as Vicryl™ (Ethicon), Monosyn™ (B Braun), catgut, oxidized regenerated cellulose, oxidized cellulose, oxidized cotton and the like, which have known well-established biodegradability patterns in the stomach and the intestines, are completely biocompatible upon ingestion, can have anti-inflammatory and antiseptic properties, and can be compressed to fit in an ingestible capsule.

The saclike member as shown in FIG. 4 can be made from permeable biodegradable mesh such as Vicryl™ Knitted Mesh by Ethicon, Curacel™ by CuraMedical, or Safil™ Mesh by B Braun and the radial fibers can be made, for example, from absorbable surgical suture such as Vicryl™, PDS II™ (Ethicon), catgut, regenerated oxidized cellulose, oxidized cellulose, oxidized cotton, or Monosyn™ (B Braun) woven therethrough. The saclike member contains clusters or agglomerates of swellable (polymer) molecules, which swell significantly when in contact with gastric liquid, thus making it impossible to exit the stomach upon ingestion. The saclike member and the radial fibers thereon are biodegradable, hence when the fibers begin to disintegrate the volume of the saclike member collapses, it loses its integrity due to the gastric peristaltic forces, and the agglomerates are released. As mentioned, the fibers can also have anti-inflammatory and antiseptic properties which can be useful not only for preventing mucosal injuries due to the presence of the bezoar in the lumen of a given gastrointestinal organ, but also to help with disorders like Crohn's disease, irritable bowel syndrome, colitis, and the like. The agglomerates comprise a swellable material selected from the group consisting of a swelling bentonite, microcrystalline hydrogels, polyolefins and various mixtures thereof. Other swellable materials that could be used include, by are not limited to, other natural clays, polyvinyl alcohol, poly(ethyloxazoline), polyvinylacetate-polyvinylalcohol copolymers, poly(2-hydroxyethylacrylate), poly(2-hydroxyethylmethacrylate), polyacrylic acid, and copolymers thereof, polysaccharides, water soluble proteins, alginates, polynucleic acids, or a combination thereof. Each swollen individual molecule cluster does not exceed 1 cm in diameter, so that such clusters can easily individually pass the pylorus and be expelled through the gastrointestinal tract after the disintegration of the container. Furthermore, if desired, the aggregates comprise a swellable material that is also biodegradable, thereby further facilitating each clusters passage through the intestines. It is understood that a variety of other biocompatible super-absorbent polymers known in the art can be used to form the clusters of the present invention, for example, polymers of poly(2-hydroxyethyl methacrylate) by Aldrich, Milwaukee, Wis., or of polyacrylamide, or of an appropriately cross-linked salt of the poly(acrylic acid) (for example, one produced by Wako Pure Chemical Industries, Japan) which expand adequately in low pH environment.

As mentioned before, in all these embodiments at least one fiber, fiber configuration, or combination thereof utilized to form the at least one bezoar in a given gastrointestinal organ may or may not be impregnated with at least one specific medicinal substance for slow release, or with at least one substance that can absorb at least one unwanted or harmful substance from the gastrointestinal liquids in the given organ. The at least one medicinal substance can include, but is not limited to, antibiotics such as erythromycin, antifungal medications such as fluconazole, antiacid medications such as omeprazole, and the like. The at least one substance that can absorb at least one unwanted or harmful substance can include but is not limited to chitosan, orlistat, and the like.

While the invention has been described in conjunction with the disclosed embodiments, it will be understood that the invention is not intended to be limited to these embodiments. On the contrary, the current protection is intended to cover alternatives, modifications and equivalents, which may be included within the spirit and scope of the invention. Various modifications will remain readily apparent to those skilled in the art.

What is claimed is:

1. A bezoar-forming unit for forming at least one temporary bezoar in a gastrointestinal organ of an animal, including a mammal, to fill a space in the organ, the bezoar-forming unit comprising:
   (a) at least one ingestible disintegrable capsule configured to disintegrate within the gastrointestinal organ subsequent to ingestion of said at least one ingestible disintegrable capsule;
   (b) a plurality of fibers stored in a folded condition within the at least one ingestible disintegrable capsule in an untangled state with one another, the plurality of fibers being of sufficient length to become entangled with one another when released from the folded condition, whereby post-ingestion disintegration of said at least one ingestible capsule results in releasing of the plurality of fibers from the ingestible capsule, unfolding of the plurality of fibers into larger dimensions within the gastrointestinal organ, and in situ tangling between said released and unfolded plurality of fibers due to natural spontaneously existing motility of the gastrointestinal organ, thereby causing in situ formation of at least one temporary bezoar through said tangling; and
   (c) a mechanism to disintegrate the at least one temporary bezoar after a predetermined amount of time.

2. The bezoar-forming unit as claimed in claim 1, whereby when the bezoar is formed it is sufficiently large so as to be retained in the gastrointestinal organ.

3. The bezoar-forming unit as claimed in claim 1, wherein the plurality of fibers comprises a material that is biodegradable over time.

4. The bezoar-forming unit as claimed in claim 1, wherein the plurality of fibers comprises a material that can act as an anti-inflammatory agent for the gastrointestinal mucosa.

5. The bezoar-forming unit as claimed in claim 1, wherein the plurality of fibers comprises a material that is degradable by a specific substance or combination of substances.

6. The bezoar-forming unit as claimed in claim 1, wherein the plurality of fibers has been impregnated with at least one specific medicinal substance for release in the gastrointestinal organ.

7. The bezoar-forming unit as claimed in claim 1, wherein the plurality of fibers has been impregnated with at least one substance that can absorb and retain at least one unwanted substance from the gastrointestinal liquid of the gastrointestinal organ.

8. A method for forming a temporary bezoar in a gastrointestinal organ of an animal, including a mammal, comprising:
   administering to the animal or mammal at least one ingestible disintegrable capsule containing a plurality of fibers in a folded condition and an untangled state with one another, the plurality of fibers being of sufficient length to become entangled with one another when released from the folded condition, whereupon each of the plurality of fibers unfolds from a first dimension to a larger second dimension; and
   allowing the at least one ingestible disintegrable capsule to disintegrate within the targeted gastrointestinal organ and release the plurality of fibers from the folded condition, thereby allowing unfolding of the plurality of fibers from the first dimension to the larger second dimension; and
   allowing entangling of the released, unfolded plurality of fibers with one another within the targeted gastrointestinal organ as a result of spontaneously existing motility of the targeted gastrointestinal organ;
   wherein the in-situ tangling of the said plurality of fibers forms at least one temporary bezoar of sufficient dimensions that preclude said at least one temporary bezoar from exiting the targeted gastrointestinal organ.

9. The method as claimed in claim 8, further comprising:
   allowing the at least one temporary bezoar to disintegrate in the gastrointestinal organ either naturally or by external stimulus, resulting in physical expulsion of remnants of the disintegrated at least one temporary bezoar when the therapy is to be discontinued.

10. The method as claimed in claim 8, wherein the at least one ingestible disintegrable capsule is administered orally.

11. The method as claimed in claim 8, wherein the at least one temporary bezoar is administered according to a predetermined dosing regimen.

12. A bezoar-forming unit for forming at least one temporary bezoar in a gastrointestinal organ of an animal, including a mammal, to fill a space in the organ, the bezoar-forming unit comprising:
- (a) at least one ingestible disintegrable capsule configured to disintegrate within the gastrointestinal organ subsequent to ingestion of said at least one ingestible disintegrable capsule; said ingestible disintegrable capsule encapsulating a permeable saclike member; wherein said saclike member contains a plurality of swellable polymers and has radial outwardly-pointing fibers attached to an outer surface of the saclike member;
- (b) upon administration in a given gastrointestinal organ, the capsule dissolves and the saclike member expands to a second dimension; the radial fibers are unfolded and untangled;
- (c) after a predetermined amount of time, the second dimension of the saclike member forms a bezoar in a third dimension; wherein the fibers are formed around the swellable polymer and entangled with one another in the third dimension.

* * * * *